(12) United States Patent
Hari

(10) Patent No.: US 12,097,230 B2
(45) Date of Patent: Sep. 24, 2024

(54) METHOD AND COMPOSITION FOR TREATING POST OPERATIVE CONDITIONS

(71) Applicant: Bright Green Corporation, Wilmington, DE (US)

(72) Inventor: V. Hari, Orlando, FL (US)

(73) Assignee: Bright Green Corporation, Wilmington, DE (US)

( * ) Notice: Subject to any disclaimer, the term of this patent is extended or adjusted under 35 U.S.C. 154(b) by 0 days.

(21) Appl. No.: 17/589,005

(22) Filed: Jan. 31, 2022

(65) Prior Publication Data

US 2023/0241145 A1    Aug. 3, 2023

(51) Int. Cl.
| | |
|---|---|
| *A61K 36/185* | (2006.01) |
| *A23L 2/52* | (2006.01) |
| *A23L 33/105* | (2016.01) |
| *A61K 9/00* | (2006.01) |
| *A61K 31/05* | (2006.01) |
| *A61K 31/352* | (2006.01) |

(52) U.S. Cl.
CPC .............. *A61K 36/185* (2013.01); *A23L 2/52* (2013.01); *A23L 33/105* (2016.08); *A61K 9/0095* (2013.01); *A61K 31/05* (2013.01); *A61K 31/352* (2013.01); *A23V 2002/00* (2013.01)

(58) Field of Classification Search
None
See application file for complete search history.

(56) References Cited

FOREIGN PATENT DOCUMENTS

CN    114344422 A  *  4/2022

* cited by examiner

*Primary Examiner* — Michael V Meller
(74) *Attorney, Agent, or Firm* — Carlson, Gaskey & Olds, P.C.

(57) ABSTRACT

An example method of treating or preventing post-operative delirium and cognitive dysfunction and other complications in patients includes administering to a patient a pharmaceutical composition. The composition includes one or more cannabinoid-containing plant compositions having a cannabinoid-containing fraction and a non-cannabinoid containing fraction. The cannabinoid-containing fraction includes *Cannabis sativa* from *C. Indica, C. Ruderalis* and their hybrids and various sub species and strains. The non-cannabinoid containing fraction from a *Cannabis sativa* L. plant and its various sub species and strains.

1 Claim, No Drawings

METHOD AND COMPOSITION FOR TREATING POST OPERATIVE CONDITIONS

BACKGROUND

The present invention relates to the use of cannabinoid-containing plant extracts in the prevention and/or treatment of post-operative delirium and cognitive dysfunction and resultant complications.

*Cannabis sativa* including *C. Indica, C. ruderalis* and their various sub species, varieties, hybrids, and eco-bio types contain different quantities of about 90 Phyto-Cannabinoids. Among these are tetrahydrocannabinol (THC) and cannabidiol (CBD), as well as other Cannabinoids, have been used to treat medical conditions or for their calming effects.

SUMMARY

An example method of treating or preventing post-operative delirium and cognitive dysfunction and other complications in patients includes administering to a patient a pharmaceutical composition. The composition includes one or more cannabinoid-containing plant compositions having a cannabinoid-containing fraction and a non-cannabinoid containing fraction. The cannabinoid-containing fraction includes *Cannabis sativa* from *C. Indica, C. Ruderalis* and their hybrids and various sub species and strains. The non-cannabinoid containing fraction from a *Cannabis sativa* L. plant and its various sub species and strains.

An oral composition includes one or more cannabinoid-containing plant extracts having a cannabinoid-containing fraction from *Cannabis sativa* including *C. Indica, C. Ruderalis* and their hybrids and various sub species and strains and a non-cannabinoid containing fraction from a *Cannabis sativa* L. plant and its various sub species and strains.

DETAILED DESCRIPTION

Palatable oral compositions having *cannabis* oil can be used to treat multiple medical conditions. In this disclosure, example oral compositions include *Cannabis* plant extracts with resin and oil containing cannabinoids consumed in a palatable pharmaceutical beverage formulation or other oral formulations for prevention and treatment of post-operative delirium and cognitive dysfunction and complications thereof. The composition can include a fraction with one or more of cannabinoids including resin, oil from *Cannabis* species and another fraction without cannabinoids.

The composition disclosed herein can treat post-operative delirium and cognitive dysfunction and other complications in all human subjects undergoing surgery. The method includes administering to a patient an oral pharmaceutical composition having one or more cannabinoid-containing plant compositions. The one or more cannabinoid-containing plant composition includes a cannabinoid-containing fraction from *Cannabis sativa* with *C. Indica, C. Ruderalis* and their hybrids and various sub species and strains and a non-cannabinoid containing fraction from the plant *Cannabis sativa* L. and its various sub species and strains.

In one example, a ratio of the cannabinoid-containing fraction to the non-cannabinoid containing fraction is varied. The cannabinoid-containing fraction can include one or more of delta tetrahydrocannabinol (delta THC), cannabidiol (CBD), cannabigerol (CBG), cannabichromene (CBC), tetrahydrocannbidivarin (THCV), tetrahydrocannabinol acid (THCA), cannabidivarin (CBDV), cannabidiolic acid (CBDA), or other un-named cannabinoids. The non-cannabinoid containing fraction can include one or more of terpenes, sterols, triglycerides, alkanes, squalling, tocopherols, carotenoids, chlorophyll, flavonoid glycosides, alkaloids, or other phytochemicals. In one example, the cannabinoid-containing fraction is predominantly cannabidiol (CBD) and in another example, the cannabinoid-containing fraction is predominantly tetrahydrocannabinol (THC). Alternatively, the cannabinoid-containing fraction could include a combination of a cannabidiol (CBD) containing plant extract and a tetrahydrocannabinol (THC) containing plant extract.

Additionally, the cannabinoid-containing fraction can include one or more *cannabis* based medicine extracts (CBME) with the one or more CBME including all of the naturally extracted *cannabis* plant components. The naturally extracted *cannabis* plant components can include any one of the following: delta tetrahydrocannabinol (delta THC); cannabidiol (CBD), cannabigerol (CBG); cannabichromene (CBC); tetrahydrocannbidivarin (THCV); tetrahydrocannabinol acid (THCA); cannabidivarin (CBDV), cannabidiolic acid (CBDA), or other un-named cannabinoids, terpenes, alkaloids, sterols, triglycerides, alkanes, squalling, tocopherols, carotenoids, chlorophyll, flavonoid glycosides and other phytochemicals.

Furthermore, the one or more cannabinoid-containing plant extract can include a major cannabinoid, a minor cannabinoid, one or more other cannabinoids, and one or more other minor plant derived components. The other minor plant derived components include at least one of sterols, triglycerides, alkanes, squalling, tocopherols, carotenoids, chlorophyll, flavonoid glycosides, alkaloids, or other phytochemicals. The major cannabinoids include tetrahydrocannabinol (THC); cannabidiol (CBD). The minor cannabinoids can include cannabinol (CBN), cannabichromene (CBC), cannabigerol (CBG), cannabidioloic acid (CBDA), cannabigerolic acid (CBGA), tetrahydrocannabinolic acid (THCA), cannabinolic acid (CBNA), cannabidivarin (CBDV), tetrahydrocannabivarin (THCV), cannabigerovarin (CBGV), cannabichromevarin (CBCV), and others.

Although the different non-limiting examples are illustrated as having specific components, the examples of this disclosure are not limited to those particular combinations. It is possible to use some of the components or features from any of the non-limiting examples in combination with features or components from any of the other non-limiting examples.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claim should be studied to determine the true scope and content of this disclosure.

What is claimed is:

1. A method of treating post-operative delirium in a human in need thereof consisting essentially of:
    administering to the human in need thereof therapeutically effective amounts of *Cannabis sativa, Cannabis*

*indica*, and *Cannabis ruderalis* to effectively treat the post-operative delirium in the human in need thereof.

\* \* \* \* \*